United States Patent [19]
Goel et al.

[11] Patent Number: 5,929,064
[45] Date of Patent: Jul. 27, 1999

[54] AMINO ACID COMPLEXES OF COBALT (III) MESOPORPHYRIN IX AND COBALT (III) PROTOPORPHYRIN IX

[75] Inventors: Om P. Goel; Stephen J. Johnson; Lawrence D. Wise, all of Ann Arbor, Mich.

[73] Assignee: Warner-Lambert Company, Morris Plains, N.J.

[21] Appl. No.: 09/011,007

[22] PCT Filed: Jul. 16, 1996

[86] PCT No.: PCT/US96/11808

§ 371 Date: Feb. 2, 1998

§ 102(e) Date: Feb. 2, 1998

[87] PCT Pub. No.: WO97/05152

PCT Pub. Date: Feb. 13, 1997

Related U.S. Application Data

[60] Provisional application No. 60/002,680, Aug. 2, 1995.

[51] Int. Cl.$^6$ ............... A61K 31/555; C07D 487/22
[52] U.S. Cl. ............... 514/185; 514/501; 540/145; 556/148
[58] Field of Search ............... 540/145; 514/501, 514/185; 556/148

[56] References Cited

U.S. PATENT DOCUMENTS

| | | | |
|---|---|---|---|
| 4,393,071 | 7/1983 | Fujii et al. | 424/274 |
| 4,619,923 | 10/1986 | Kappas et al. | 514/185 |
| 4,657,902 | 4/1987 | Kappas et al. | 514/185 |
| 4,782,049 | 11/1988 | Kappas et al. | 514/185 |
| 4,916,221 | 4/1990 | Kumadaki et al. | 540/145 |
| 4,948,792 | 8/1990 | Kappas et al. | 514/185 |
| 4,961,920 | 10/1990 | Ward | 424/9 |
| 5,149,697 | 9/1992 | Johnson et al. | 514/185 |
| 5,192,757 | 3/1993 | Johnson et al. | 514/185 |
| 5,422,093 | 6/1995 | Kennedy et al. | 424/9.61 |

OTHER PUBLICATIONS

Chemical Abstracts, vol. 78, No. 26, 1993 "Metal Ions and Hydrogen Peroxide, XXVII. Inhibition of the Catalase Activity of Cobalt (III)–Hematoporphyrin by Amino Acids, Adenine, and Related Ligands. Stability of the Inhibitor Adducts", Abstract No. 164749n, Waldmeier, P. et al.

Chemical Abstracts, vol. 88, No. 25, 1978, "Structural Studies on Metalloporphyrins. Part IV. Determination of the Conformation of Amines and Amino–Esters Complexed with Cobalt (III) Porphyrins", Abstract No. 189886z, Gouedard, M., et al.

Chemical Abstracts, vol. 89, No. 1, 1978, "Structural Studies on Metalloporphyrins. Part I. Preparation and Nuclear Magnetic Resonance Spectra of Complexes of Amines and Amino–Esters with Cobalt (III) Porphyrins", Abstract No. 6312n, Gouedard, M., et al.

Chemical Abstracts, vol. 98, No. 21, 1983, "Structural Studies of Metalloporphyrins. VIII. NMR Evidence for Planar Chirality in Natural Porphyrins", Abstract No. 178604m, Gaudemer, A., et al.

PCT International Search Report, PCT/US96/11808 (1996).

Inernal Medicine, 4th Edition, Editor–in–Chief Jay Stein, Chapters 71–72, pp. 699–715.

*Primary Examiner*—Porfirio Nazario-Gonzalez
*Attorney, Agent, or Firm*—Francis J. Tinney

[57] ABSTRACT

Amino acid complexes of cobalt (III) mesoporphyrin IX and cobalt (III) protoporphyrin IX are described, as well as methods for the preparation and pharmaceutical composition of same, which are useful as antiobesity agents and for the treatment of cyanide poisoning, neonatal hyperbilirubinemia, and cancer.

16 Claims, 5 Drawing Sheets

AMINO ACID COMPLEXES OF COBALT (III) MESOPORPHYRIN IX AND COBALT (III) PROTOPORPHYRIN IX

CROSS-REFERENCES TO RELATED APPLICATIONS

This application was filed as a request for U.S. examination under 35 U.S.C. § 371 of International application No. PCT/US96/11808 filed Jul. 16, 1996. This application claims benefit of provisional application 60/002,680 filed Aug. 2, 1995.

BACKGROUND TO THE INVENTION

The present invention relates to amino acid complexes of cobalt (III) mesoporphyrin IX and cobalt (III) protoporphyrin IX useful as pharmaceutical agents, to methods for their production, to pharmaceutical compositions which include these compounds and a pharmaceutically acceptable carrier, and to pharmaceutical methods of treatment. The novel compounds of the present invention are useful as antiobesity agents and can also be useful for treatment of cyanide poisoning, neonatal hyperbilirubinemia and cancer.

Cobalt porphyrins are known to have various endocrine activities including the regulation of food intake for controlling obesity [Galbraith R. A. and Kappas A., *Proc. Natl. Acad. Sci. U.S.A.*, 1989;86:7653–7657; Galbraith R. A. and Krey L. C., *Neuroendocrinology*, 1989;49:641–648; Galbraith R. A., et al., *Pharmacoloy*, 1987;34:241–249; Galbraith R. A. and Jellinck P. H., *Biochemical and Biophysical Research Communications*, 1987;145(1):376–383; Drummond G. S., et al., *Proc, Natl. Acad. Sci. U.S.A.*, 1982;79:2384–2388; Smith T. J., et al., *Pharmacology*, 1986;34(9):9–16].

Phototherapeutic porphyrin-type dimers are disclosed in U.S. Pat. No. 4,961,920. Various porphyrins are disclosed in U.S. Pat. No. 4,393,071 to be useful in treatment of tumors; in U.S. Pat. No. 4,619,923 to control tryptophan metabolism; in U.S. Pat. No. 4,657,902 to inhibit heme metabolism; and in U.S. Pat. No. 4,782,049 to treat psoriasis. Methods of suppressing the immune system with cobalt protoporpyrins are described in U.S. Pat. No. 4,948,792; International Published Patent Application WO 87/04927 and for weight loss in International Published Patent Application WO 90/09173. The adjustment of testosterone levels in rats by the administration of cobalt mesoporphyrin is disclosed by Galbraith R. A., et al., *J. Steroid Biochem.*, 1989;32(3):421–427. Several related cobalt porphyrins are disclosed in U.S. Pat. No. 5,149,697 and U.S. Pat. No. 5,192,757 to be antiobesity agents.

The preparations of some amino acid ester complexes with cobalt (III) deuteroporphyrin dimethyl ester and with Co(III) tetraphenylporphyrin in nonpolar organic solvents are described by Gouedard M., et al., *J. Chem. Res.*, 1978:36–37.

We have surprisingly and unexpectedly found that common amino acid salts in water will react with cobalt (II) mesoporphyrin IX and cobalt (II) protoporphyrin to produce water-soluble complexes of cobalt (III) mesoporphyrin IX and cobalt (III) protoporphyrin IX that are effective antiobesity agents. High water solubility allows therapeutically useful dose volumes when the compounds are administered by injection. Additionally, this reduces depot effect at the injection site and has the potential for providing greater initial potency with shorter duration of action.

SUMMARY OF THE INVENTION

Accordingly, the present invention is a compound of Formula I

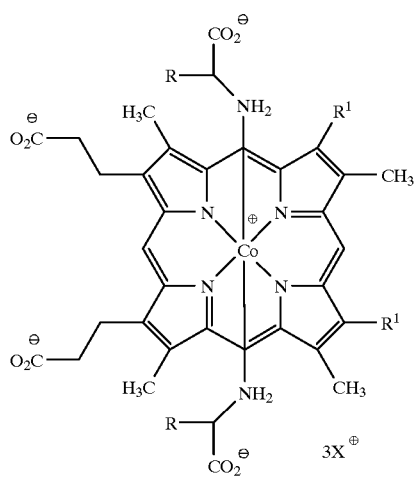

wherein R is

H, alkyl, alkenyl, cycloalkyl, cycloalkylalkyl, aryl, arylalkyl, heteroaryl, heteroarylalkyl, —$(CH_2)_n$—$R^2$ wherein $R^2$ is OH, —S-alkyl, —$NH_2$,

—NH—C(=NH)—$NH_2$, —NH—C(=O)—$NH_2$, —$CO_2H$, or

—$CONH_2$, and n is zero or an integer of 1 to 4, or

—$(CH)_n$-alkyl, wherein n is as defined above;
|
OH $R^1$ is —$CH_2CH_3$ or —CH=$CH_2$; and X is hydrogen or a pharmaceutically acceptable cation.

A further embodiment of the invention is a compound of Formula II

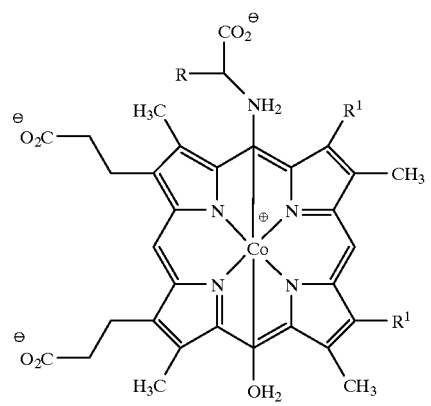

wherein R is H, alkyl,
alkenyl,
cycloalkyl,
cycloalkylalkyl,
aryl,
arylalkyl,
heteroaryl,
heteroarylalkyl,
—(CH$_2$)$_n$—R$^2$ wherein R$^2$ is

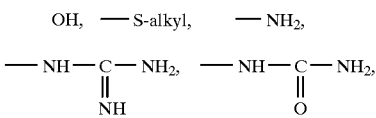

—CO$_2$H, or
—CONH$_2$, and
n is zero or an integer of 1 to 4, or

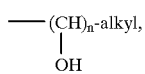

wherein n is as defined above;
R$^1$ is —CH$_2$CH$_3$ or —CH=CH$_2$; and
X is hydrogen or a pharmaceutically acceptable cation.

The compounds of Formula I and Formula II are useful as antiobesity agents and are useful for treating obesity. They are also useful for the treatment of cyanide poisoning, neonatal hyperbilirubinemia, and cancer.

A still further embodiment of the present invention is a pharmaceutical composition for administering an effective amount of a compound of Formula I or Formula II in unit dosage form in the treatment methods mentioned above. Finally, the present invention is directed to methods for production of a compound of Formula I and Formula II.

BRIEF DESCRIPTION OF THE DRAWINGS

The invention is further described by the following non-limiting examples which refer to the accompanying FIGS. 1 to 5, short particulars of which are given below.

DETAILED DESCRIPTION OF THE INVENTION

Figure 1:
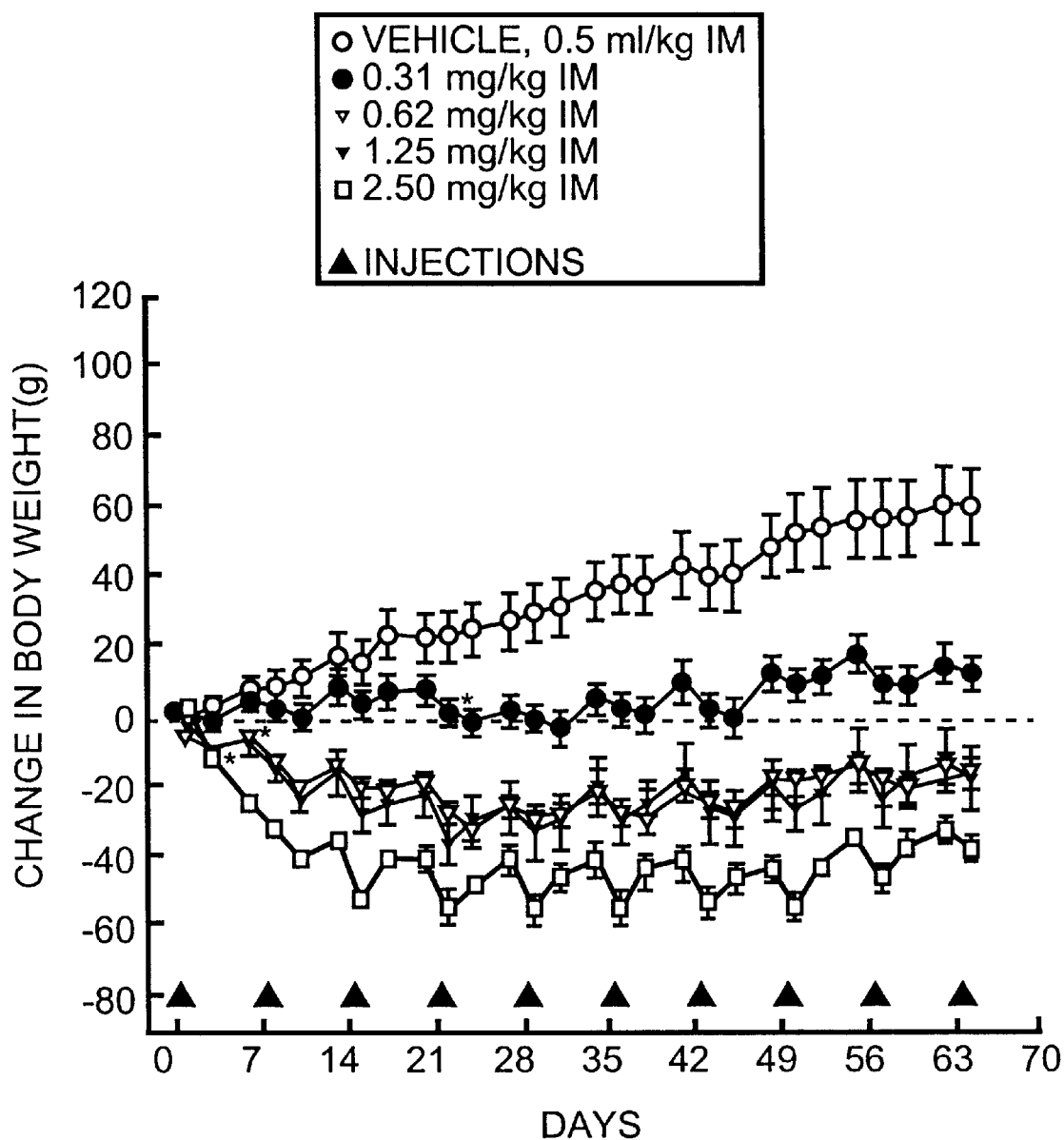
FIG. 1. Effect of IM Injection of Example 1 on Weight Gain in Normal Rats

In the compounds of Formulas I and II, the term "alkyl" means a straight or branced hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "alkenyl" means a straight or branched unsaturated hydrocarbon radical having from 2 to 6 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a naphthyl group, a biphenyl group, a pyrenyl group, an anthracenyl group, or a fluorenyl group and the like, unsubstituted or substituted by 1 to 4 substituents selected from alkyl as defined above, alkoxy as defined above, thioalkoxy as defined above, hydroxy, thiol, nitro, halogen, amino,

wherein alkyl is as defined above,

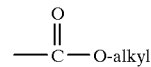

wherein alkyl is as defined above,

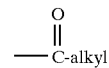

wherein alkyl is as defined above, or aryl.

The term "heteroaryl" means a heteroaromatic radical which is 2- or 3-thienyl, 2- or 3-furanyl, 2- or 3-pyrrolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino,

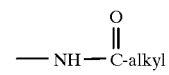

wherein alkyl is as defined above,

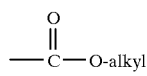

wherein alkyl is as defined above,

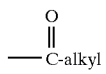

wherein alkyl is as defined above or phenyl.

The term "arylalkyl" means an aromatic radical attached to an alkyl radical wherein aryl and alkyl are as defined above, for example, benzyl, fluorenylmethyl and the like.

The term "heteroarylalkyl" means a heteroaromatic radical attached to an alkyl radical wherein heteroaryl and alkyl are as defined above.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The term "pharmaceutically acceptable cation" means a metal or amine suitable for forming a pharmaceutically acceptable base addition salt as disclosed in Berge S M, et al., "Pharmaceutical Salts", *J. of Pharma. Sci.*, 1977;66:1, for example, alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The term "host" means man and animals, particularly pets such as cats and dogs and domesticated farm animals, such as, pigs.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. Additionally, the compounds of the present invention may exist as geometric isomers. The present invention includes all cis, trans, syn, and anti isomers as well as the appropriate mixtures thereof.

A preferred compound of Formula I is one wherein

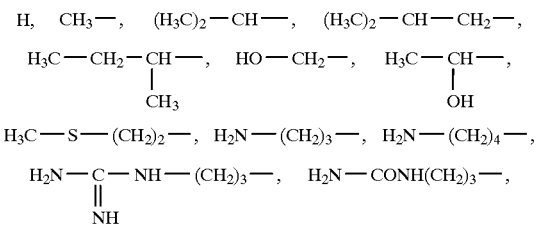

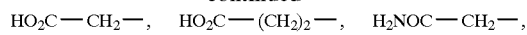

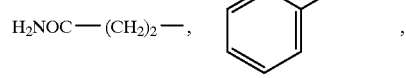

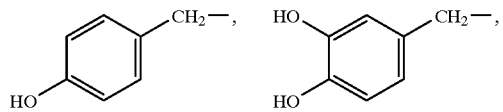

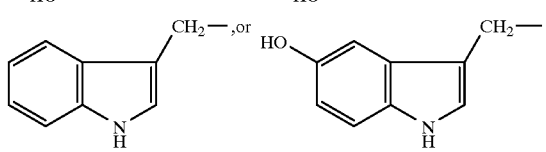

A more preferred compound of Formula I is one wherein R is

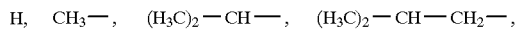

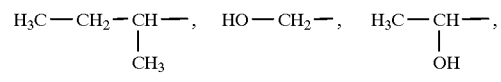

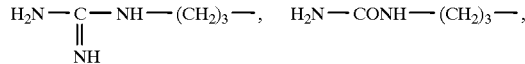

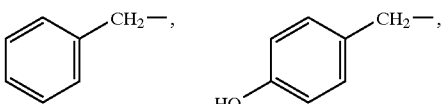

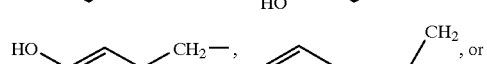

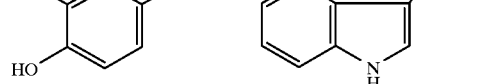

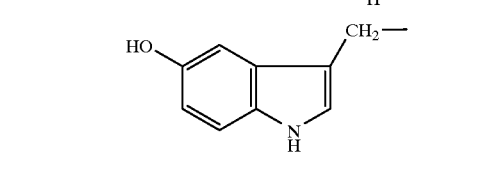

Particularly valuable are:

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(glycinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(glycinato-N)-, trihydrogen;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(alaninato-N)-, trisodium;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(serinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(lysinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(ornithinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}, N^{24}$]-bis(cirullinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(argininato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(phenylalaninato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(tyrosinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(3-hydroxytyrosinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(threoninato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(leucinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(isoleucinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(valinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(tryptophanato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(5-hydroxytryptophanato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(glycinato-N)-, trihydrogen;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(alaninato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(serinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(lysinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(ornithinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(cirullinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(argininato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(phenylalaninato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(tyrosinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(3-hydroxytyrosinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(threoninato-N)-, trisodium;

Cobaltate(3-), [7,12-diethenyl-3,8,13,17-tetramethyl-21H, 23H-porphine-2,18-dipropanoato(4-)-$N^{21},N^{22}$, $N^{23},N^{24}$]-bis(leucinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(isoleucinato-N)-, trisodium;

Cobaltate(3-), [7,12-diethenyl-3,8,13,17-tetramethyl-21H,23H-porphine-2,18-dipropanoato(4-)-$N^{21},N^{22}$, $N^{23},N^{24}$]-bis(valinato-N)-, trisodium;

Cobaltate(3-), [7,12-diethenyl-3,8,13,17-tetramethyl-21H, 23H-porphine-2,18-dipropanoato(4-)-$N^{21},N^{22}$, $N^{23},N^{24}$]-bis(tryptophanato-N)-, trisodium; and Cobaltate(3-), [7,12-diethenyl-3,8,13,17-tetramethyl-21H, 23H-porphine-2,18-dipropanoato(4-)-$N^{21},N^{22}$, $N^{23},N^{24}$]-bis(5-hydroxytryptophanato-N)-, trisodium.

Most particularly valuable is:

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(glycinato-N)-, trisodium;

Cobaltate(3-), [7,12-diethyl-3,8,13,17-tetramethyl-21H, 23H-porphine-2,18-dipropanoato(4-)-$N^{21},N^{22},N^{23}$, $N^{24}$]-bis(tryptophanato-N)-, trisodium; and Cobaltate(3-), [7,12-diethyl-3,8,13,17-tetrameethyl-21H, 23H-porphine-2,18-dipropanoato(4-)-$N^{21},N^{22},N^{23}$, $N^{24}$]-bis-(5-hydroxytryptophanato-N)-, trisodium.

A preferred compound of Formula II is one wherein R is

H,  $CH_3-$,  $(H_3C)_2-CH-$,  $(H_3C)_2-CH-CH_2-$, $H_3C-CH_2-\underset{\underset{CH_3}{|}}{CH}-$,  $HO-CH_2-$,  $H_3C-\underset{\underset{OH}{|}}{CH}-$, $H_3C-S-(CH_2)_2-$,  $H_2N-(CH_2)_3-$,  $H_2N-(CH_2)_4-$, $H_2N-\underset{\underset{NH}{\|}}{C}-NH-(CH_2)_3-$,  $H_2N-CONH(CH_2)_3-$, $HO_2C-CH_2-$,  $HO_2C-(CH_2)_2-$,  $H_2NOC-CH_2-$, $H_2NOC-(CH_2)_2-$, [benzyl group],

[4-hydroxybenzyl group], [3,4-dihydroxybenzyl group],

[indol-3-ylmethyl group], or [5-hydroxyindol-3-ylmethyl group]

A more preferred compound of Formula II is one wherein R is

H,  $CH_3-$,  $(H_3C)_2-CH-$,  $(H_3C)_2-CH-CH_2-$, $H_3C-CH_2-\underset{\underset{CH_3}{|}}{CH}-$,  $HO-CH_2-$,  $H_3C-\underset{\underset{OH}{|}}{CH}-$, $H_2N-(CH_2)_3-$,  $H_2N-(CH_2)_4-$, $H_2N-\underset{\underset{NH}{\|}}{C}-NH-(CH_2)_3-$,  $H_2N-CONH-(CH_2)_3-$,

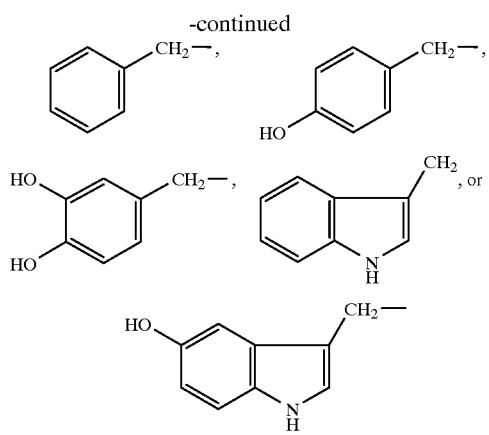

Particularly valuable is:

Cobaltate(3-), [7,12-diethyl-3,8,13,17-tetrameethyl-21H, 23H-porphine-2,18-dipropanoato(4-)-$N^{21}, N^{22}, N^{23}, N^{24}$]-monoaquato mono(glycinato-N-), disodium; and Cobaltate(3-), [7,12-diethenyl-3,8,13,17-tetramethyl-21H,23H-porphine-2,18-dipropanoato(4-)-$N^{21}, N^{22}, N^{23}, N^{24}$]-monoaquato mono(glycinato-N)-, disodium.

The compounds of Formulas I and II are valuable antiobesity agents. The tests employed indicate that compounds of Formulas I and II reduced food consumption and resulted in significant changes in body weight when administered to rats and monkeys. Selective compounds of Formulas I and II were evaluated using the following methodology and demonstrated their utility as antiobesity agents.

Biological Testing

Effect of Example 1 on Body Weight and Food Consumption in Rats and Cynomolgus Monkeys The effects of repeated intramuscular (IM) injections of Example 1 on body weight and food consumption in normal rats and genetically obese Zucker (fa/fa) rats was examined. In addition, the effects of Example 1 on body weight of cynomolgus monkeys after repeated IM injections was examined.

Methods

Normal Rat Study

Animals. Male Sprague-Dawley rats (Harlan Labs) were used for this study. Six animals were assigned to each of 5 treatments on the basis of weight. The mean body weights for the treatment groups varied from 410 to 415 g at the start of injections. Individual weights varied from 366 to 471 g. Before treatments were started, animals were acclimated for 2 weeks to powdered rat food (Purina Rat Chow 5002) and to the routine of handling and weighing 3 times a week (Monday, Wednesday, and Friday).

Drug. Example 1 was dissolved in physiologic saline (12.5 mL was added to a vial containing 62.3 mg parent compound). That reconstitution produced a concentration of 2.5 mg/0.5 mL; 0.5 mL was administered per kilogram of body weight. Further serial dilutions of 1.25, 0.625, and 0.3125 mg/0.5 mL were made from the original dilution. Saline, 0.5 mL/kg IM, was used for the vehicle-treated control. Treatments were administered Tuesday mornings between 10:30 and 11 AM. Doses were divided equally at 2 injection sites; the gluteal muscle of each hind leg were the sites of injection. The weight obtained on the Monday before treatment was used to determine the dose.

Food Consumption. Each animal was presented a food cup with a measured amount of powdered rat chow daily. Food consumption was based on the portion remaining in the cup on the following day; major spills of food were recovered and added to the cup before weighing. On Fridays the animals were given double portions of powdered chow plus 3 to 4 pellets of rat chow for each rat. The pellets were included to enable the animals to keep their incisors trimmed. Then on Sundays, animals were again given a food cup with a measured quantity of food. Food consumption was measured 5 days per week (Monday–Friday).

Significant changes in body weights and food consumption, relative to vehicle-treated controls, were determined by Student's t-test.

Zucker Rat Study

Animals and Treatments. Male Zucker (fa/fa) rats from Harlan Labs were used for this study. Animals were acclimated to individual housing and powdered rat chow for 1 month prior to treatments. Six animals were assigned to each of 4 treatment groups (saline, Example 1, 0.3125, 0.625, and 1.25 mg/kg) on the basis of weight. The starting mean body weight for the groups ranged from 719 to 725 g; individual weights varied from 629 to 913 g. One animal died before treatments were started; that position was allotted to the high dose so that rats were started on the 1.25-mg/kg dose.

Saline and Example 1 were administered IM and on Tuesdays as in the normal rat study. Daily monitoring of food consumption and monitoring of body weight were the same as the normal rat study. Significant changes were determined by Student's t-test.

Cynomolgus Monkey Study

Animals and Treatments. Male and female cynomolgus monkeys weighing from 5.12 to 11.53 kg were used for this study. Body weights and monkey chow pellet consumption was monitored for about 1 year prior to the study. Body weights were stable 2 to 3 months before treatments were started. Five animals were assigned to each of 4 treatments.

As in the Zucker rat study, treatments consisted of saline, Example 1, 0.3125, 0.625, and 1.25 mg/kg. Treatments were injected IM into the thigh muscles on Tuesdays. Doses were divided equally at 2 injection sites.

Body weights were monitored 3 times per week (Monday, Wednesday, and Friday). Significant changes in body weight were determined by Student's t-test.

Both rat studies and the monkey study were maintained for at least 70 days. The animals received at least 10 treatments over the period of 10 weeks.

Results

Normal Rat Study

After 2 to 4 treatments of Example 1, 0.625, 1.25, and 2.5 mg/kg IM, normal rats lost a significant ($p < 0.05$) amount of weight relative to vehicle-treated controls and were below their starting weights (FIG. 1). The lowered weight was then maintained despite additional treatments. The lowest dose, 0.3125 mg/kg significantly ($p < 0.05$) reduced weight gain relative to vehicle-treated controls but did not cause animals to lose below their starting weights (FIG. 1).

Figure 2:
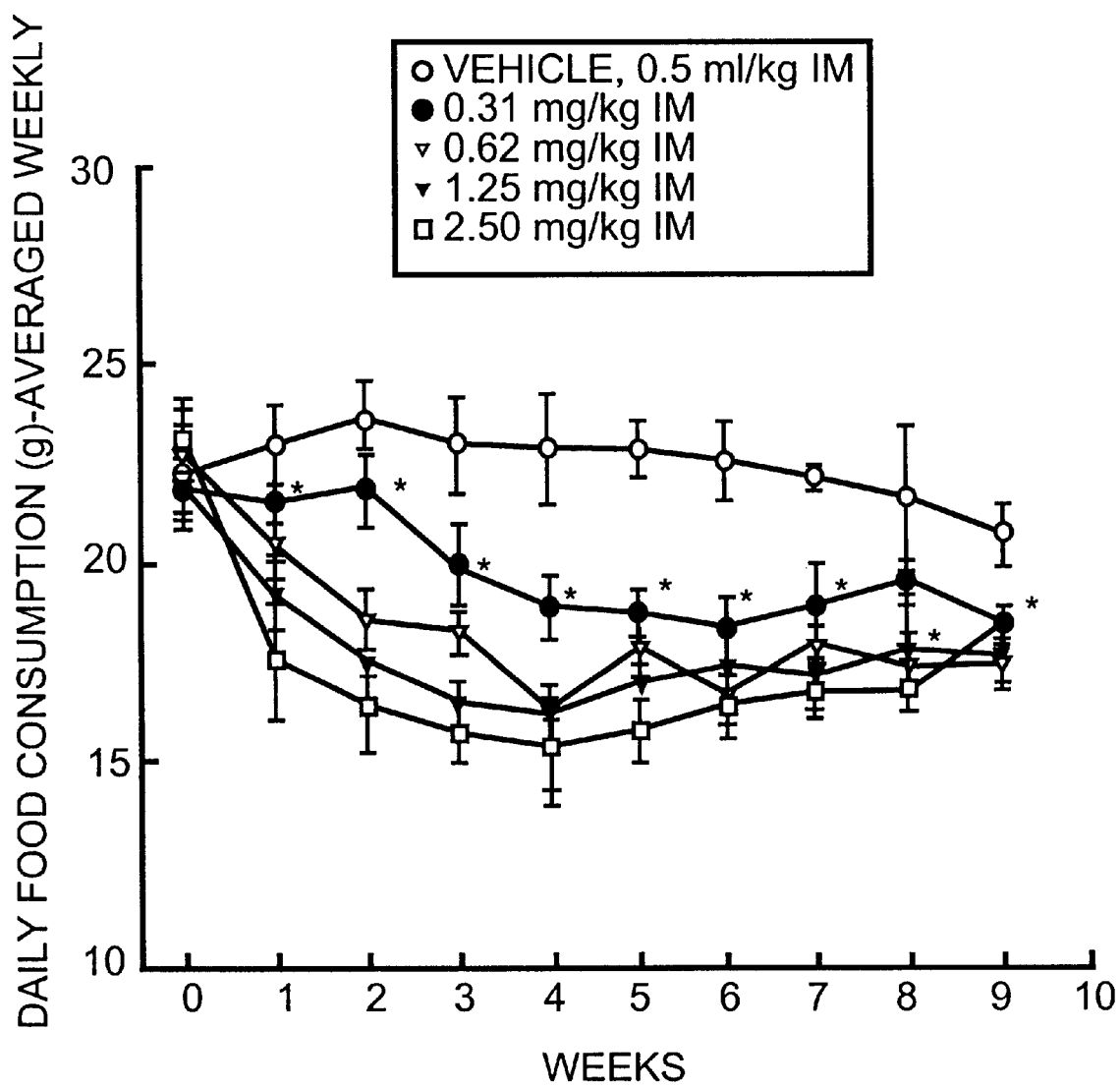
FIG. 2. Effect of IM Injection of Example 1 on Food Consumption in Normal Rats

Example 1 treatments reduced food consumption in a dose-related manner (FIG. 2). All doses produced a significant ($p < 0.05$) reduction of food intake relative to vehicle-treated controls. Diminished food intake leveled off after 2 to 4 treatments of the doses tested.

Zucker Rat Study

Figure 3:
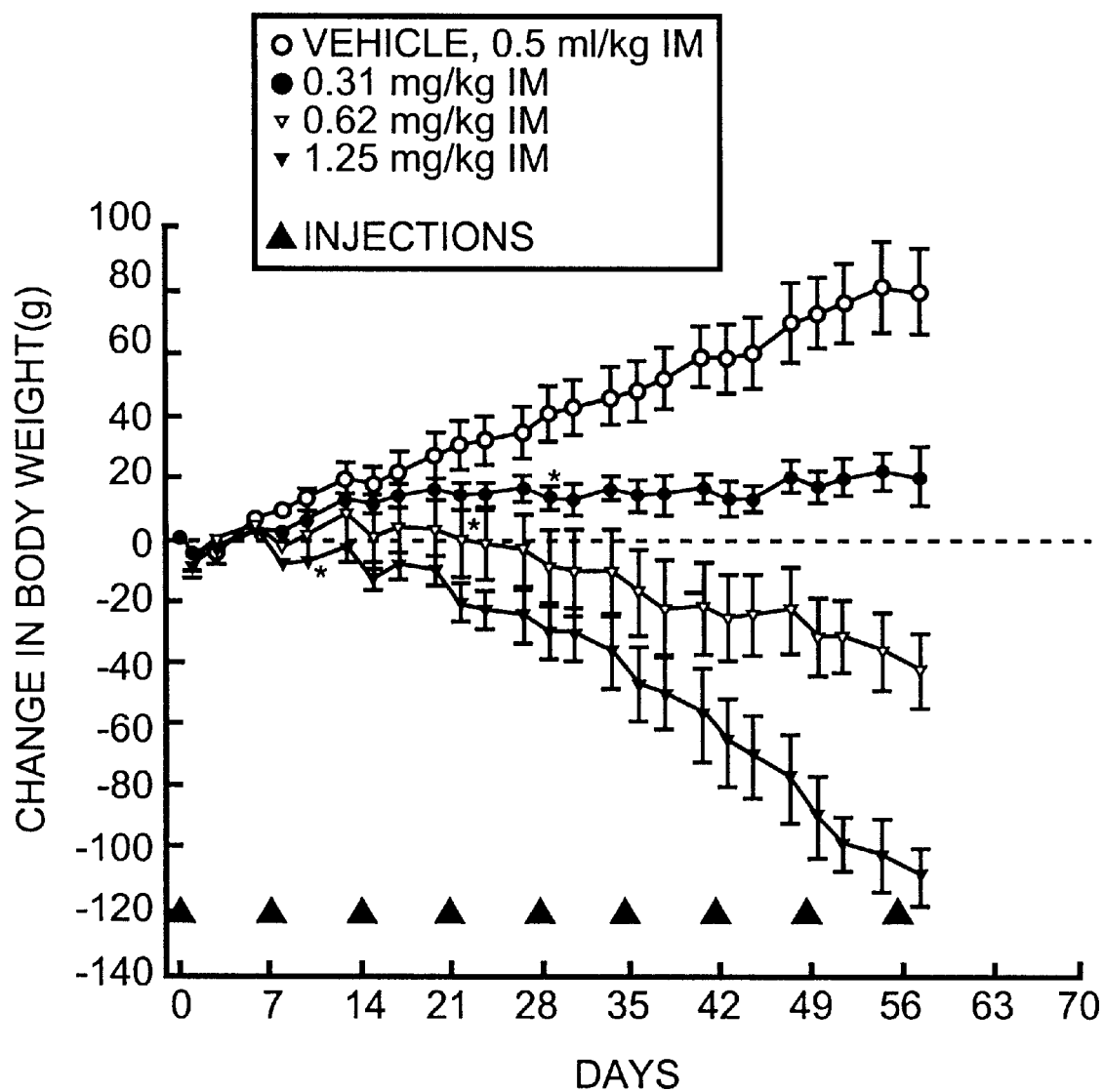
FIG. 3 Effect of IM Injection of Example 1 on Weight Gain in Zucker Rats
Figure 4:
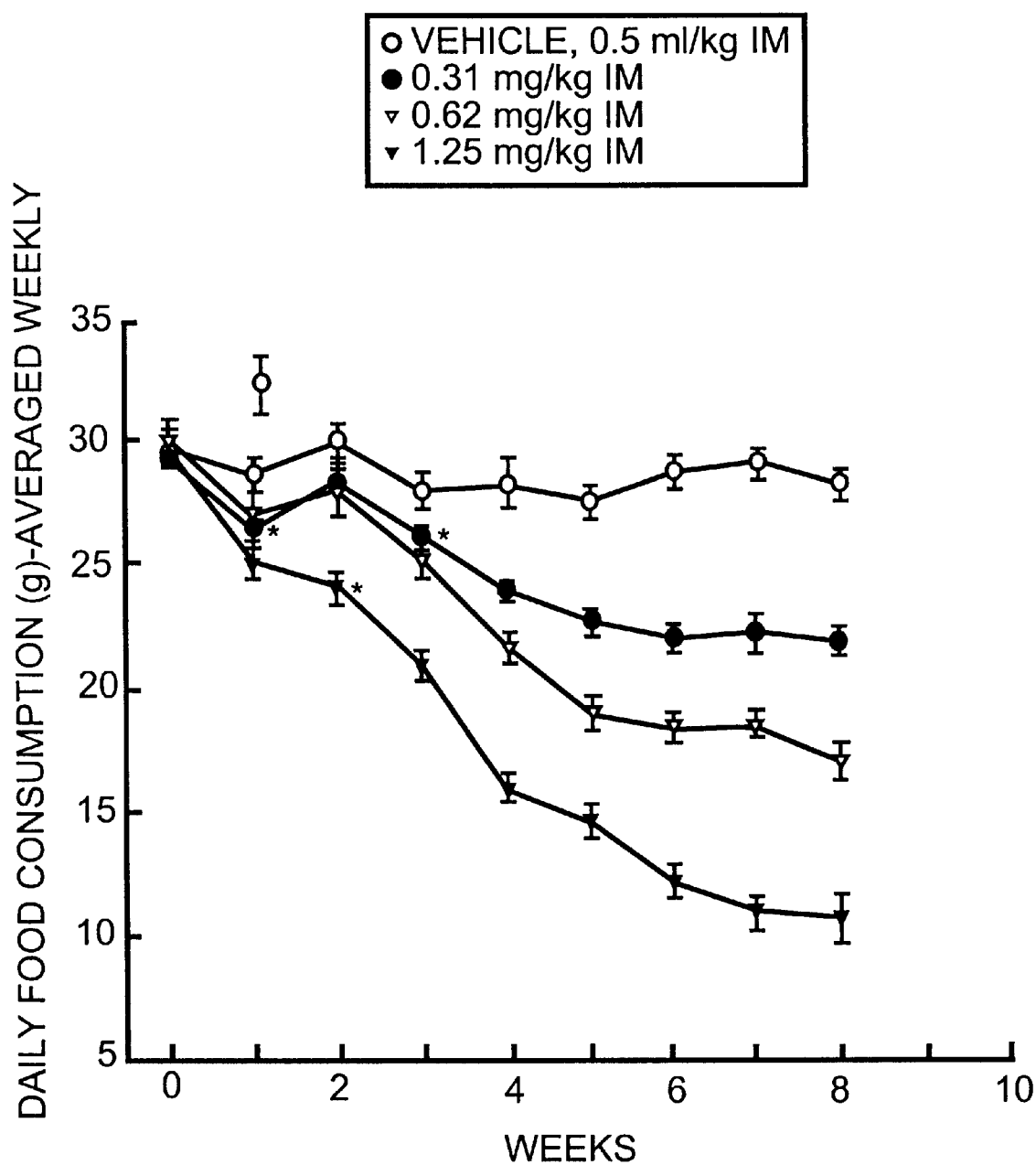
FIG. 4. Effect of IM Injection of Example 1 on Food Consumption in Zucker Rats

After 2 and 4 doses of 1.25 and 0.625 mg/kg IM of Example 1, respectively, Zucker rats lost significant ($p < 0.05$) weight relative to vehicle controls and began to fall below their starting weights (FIG. 3). In contrast to the normal rat study, Zucker rats continued to lose weight with each successive dose of 0.625 and 1.25 mg/kg. The lowest dose, 0.3125 mg/kg reduced weight gain but did not cause the animals to fall below their starting weights. Example 1 treatments significantly (p <0.05) reduced food consumption in the Zucker rats (FIG. 4). The response was dose-related and continued to diminish intake over the period of observation.

Monkey Study

Figure 5:
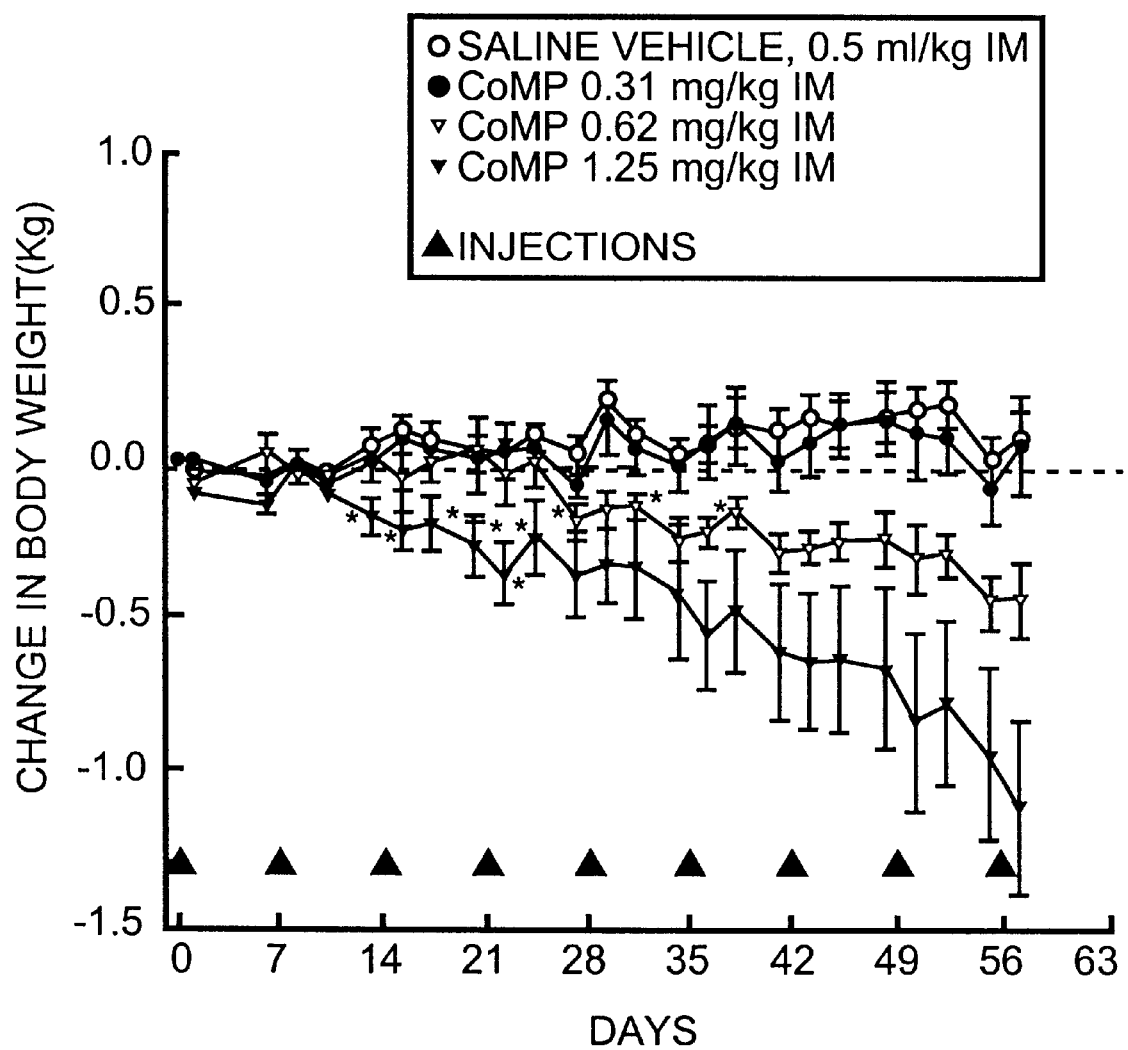
FIG. 5. Effect of IM Injection of Example I on Weight Gain in Cynomolgus Monkeys

Cynomolgus monkeys also lost a significant (p <0.05) amount of weight, relative to vehicle-treated controls, after 2 and 4 injections of 0.625 and 1.25 mg/kg IM of Example 1, respectively (FIG. 5). Interestingly, the animal with the lowest starting weight (5.12 kg) in the 1.25 mg/kg treatment group, after 9 injections, had lost the least (0.1 kg) while the heavier animals lost 0.8 to 1.78 kg. The 1.25 mg/kg group, after 9 injections, lost an average of 10% from their starting weights. The 0.3125-mg/kg dose of Example 1 was essentially without effect on body weight in cynomolgus monkeys.

A compound of Formula I

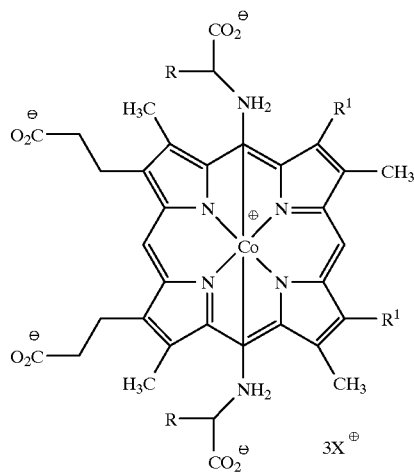

wherein R is

H, alkyl, alkenyl, cycloalkyl, cycloalkylalkyl, aryl, arylalkyl, heteroaryl, heteroarylalkyl, —$(CH_2)_n$—$R^2$ wherein $R^2$ is OH, —S-alkyl,

—$NH_2$, —NH—C(=NH)—$NH_2$, —NH—C(=O)—$NH_2$,

—$CO_2H$, or —$CONH_2$, and n is zero or an integer of 1 to 4, or

—$(CH)_n$-alkyl, wherein n is as defined above;
  |
  OH $R^1$ is —$CH_2CH_3$ or —$CH=CH_2$;

and

X is hydrogen or a pharmaceutically acceptable cation may be prepared from a compound of Formula III

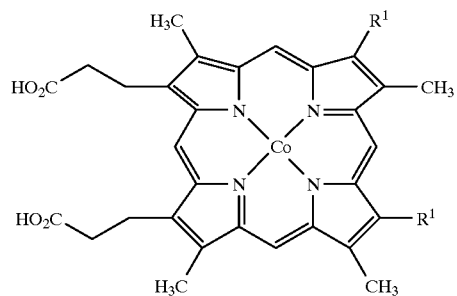

wherein $R^1$ is as defined above and two or more equivalents of a compound of Formula IV

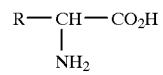

wherein R is as defined above and three or more equivalents of a base such as, for example, alkali metal, or alkaline earth metal hydroxide, carbonate, or bicarbonate or an organic amine in a solvent such as, for example, water and the like under an air or oxygen atmosphere for a sufficient time to affect dissolution and to afford after filtration and lyophilization a compound of Formula I.

A compound of Formula II

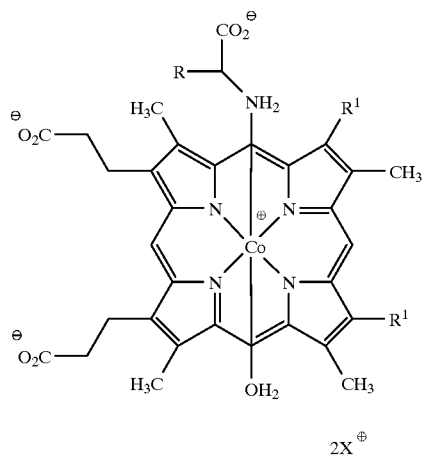

wherein R is

H, alkyl, alkenyl, cycloalkyl, cycloalkylalkyl, aryl, arylalkyl, heteroaryl, heteroarylalkyl, —$(CH_2)_n$—$R^2$ wherein $R^2$ is OH, —S-alkyl,

—$NH_2$, —NH—C(=NH)—$NH_2$, —NH—C(=O)—$NH_2$,

—$CO_2H$, or —$CONH_2$, and n is zero or an integer of 1 to 4, or

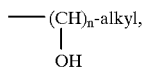

wherein n is as defined above;

R$^1$ is —CH$_2$CH$_3$ or —CH=CH$_2$; and

X is hydrogen or a pharmaceutically acceptable cation may be prepared from a solution of a compound of Formula I in water by adjusting the pH to afford a compound of Formula II.

Compounds of Formula III and Formula IV are either known or capable of being prepared by methods known in the art.

General procedures for cobalt porphyrin synthesis are disclosed in Falk J. E., "Porphyrins and Metalloporphyrins"; Elsevier Scientific Publishing Company: Amsterdam-Oxford-New York, 1975.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formulas I or II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 50 to 500 mg according to the particular application and the potency of the active component. The composition can, if desired, also contain other compatible therapeutic agents.

In therapeutic use as antiobesity agents, agents for treating cyanide poisoning, neonatal hyperbilirubinemia, and cancer, the compounds utilized in the pharmaceutical methods of this invention are administered at the initial dosage of about 0.1 mg to about 100 mg per kilogram daily. A weekly dose range of about 0.3 mg to about 3 mg per kilogram for treatment of obesity is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total weekly dosage may be divided and administered in portions during the week, if desired.

The following nonlimiting examples illustrate the inventors' preferred methods for preparing the compounds of the invention.

EXAMPLE 1

Cobalt (III) Mesoporphyrin IX bisglycinate trisodium salt (Cobaltate(3-), [7,12-diethyl-3,8,13, 17-tetramethyl-21H 23H-porphine-2,18-dipropanoato(4-)-N$^{21}$,N$^{22}$,N$^{23}$,N$^{24}$]-bis(glycinato-N)-, trisodium)

Cobalt (II) mesoporphyrin IX (cobaltate(2-),[7,12-diethyl-3,8,13,17,-tetramethyl-21H,23H-porphine2,18-dipropanoato(4-)-N$^{21}$,N$^{22}$,N$^{23}$, N$^{24}$]-dihydrogen) (Taylor, J. F., *Journal of Biological Chemistry*, 1940;135:569–595)

(35.8 mg) is stirred under an air atmosphere with a solution of glycine (8.6 mg) in 0.1M aqueous sodium hydroxide (1.72 mL) for 48 hours at room temperature. The solution is filtered through a sintered glass or PTFE frit and rinsed through with water. The filtrate is frozen then vacuum dried at 0.3 torr to give the lyophilized product (54 mg). $^1$H nmr (D$_2$O, referenced TSPA to δ 0): δ 10.63 (s, 1H), 10.58 (s, 2H), 10.54 (s, 1), 4.56 (t, 4H), 4.23 (m, 4H), 3.80 (s, 3H), 3.79 (s, 3H),3.75 (s, 3H), 3.75 (s, 3H), 3.74 (s, 3H) 3.20 (4H, t), 1.89 (t, 3H), 1.87 (t, 3H), −3.99, (t which changes to singlet as −5.96 peak disappears, 4H), −5.52 (t, disappears over time due to deuterium exchange). UV/Vis in aqueous 10$^{-2}$M sodium glycinate and 10$^{-2}$M glycine buffer: $\lambda_{max}$ 412 nm (molar absorptivity 1.66×10$^5$).

Analysis calculated for $C_{34}H_{34}N_4O_4Co_1(C_2H_4N_1O_2)_2$ Na$_3$.8H$_2$O: C, 46.44; H, 5.95; N, 8.55; Na, 7.02; Co, 6.00; H$_2$O, 14.6%. Found: C, 46.16; H, 5.86; N, 8.39; Na, 7.25; Co, 6.13; H$_2$O by Karl Fisher 13.26%.

The dissolution time may be reduced substantially by warming the stirred mixture at 50° C. to 70° C.

EXAMPLE 2

Buffered Injectable Formulation of Cobalt (III) Mesoporphyrin IX Bisglycinate Trisodium Salt The complex of Example 1 may be prepared using excess glycine and sodium hydroxide, for example, 3 equivalents of glycine and 3.5 equivalents of sodium hydroxide, in which case the product is obtained as a mixture with glycine and sodium glycinate. This method produces a buffered formulation with pH 9.7. The ratio of excess glycine and sodium hydroxide may be varied to produce solutions of pH 8 to pH 10.

EXAMPLE 3

Mixture of Cobalt (III) Mesoporphyrin IX bisglycinate and Cobalt (III) Mesoporphyrin IX monoglycinate monowater complex, Cobaltate(3-), [7,12-diethyl-3,8,13,17-tetramethyl-21H,23H-porphine-2,18-dipropanoato(4-)-N$^{21}$,N$^{22}$,N$^{23}$,N$^{24}$]-monoaquato mono(glycinato-N)-disodium)

The acidity of a solution of Cobalt (III) mesoporphyrin (Example 1) is increased by the addition of phosphate buffer at pH 7.0. The ratio of bisglycinate to monoglycinate is approximately 5:1, depending somewhat on the concentration of the solution.

General procedure for preparation of Cobalt III Mesoporphyrin IX amino acid, trisodium salt complexes The complexes can be prepared by treating cobalt (II) mesoporphyrin IX or cobalt (II) protoporphyrin IX (cobaltate(2-), [7,12-diethenyl-3,8,13,17-tetramethyl-21H,23-porphine-2,18-dipropanoato(4-)-N$^{21}$,N$^{22}$,N$^{23}$,N$^{24}$]-dihydrogen) (Treibs, A., *Liebigs Ann. Chem.*, 1969;728:115–148) with two or more equivalents of an amino acid along with three or more equivalents of sodium hydroxide in water under an air or oxygen atmosphere for sufficient time to affect dissolution. The solution may be filtered and lyophilized to give solid material.

Additionally, other base salt complexes can be prepared by treating cobalt (II) mesoporphyrin IX or cobalt (II) protoporphyrin IX with two or more eqivalents of an amino acid along with three or more eqivalents of a base, such as, for example, alkali and alkaline earth metal hydroxides and carbonates or organic amines in water under an air or oxygen atmosphere for sufficient time to affect dissolution. The solution may be filtered and lyophilized to give solid material.

Using the general process described above and using appropriate starting materials, the corresponding compounds of Formulas I and II (Examples 4–32) may be prepared as follows:

EXAMPLE 4

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(alaninato-N)-, trisodium

EXAMPLE 5

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(serinato-N)-, trisodium

EXAMPLE 6

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(lysinato-N)-, trisodium

EXAMPLE 7

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(ornithinato-N)-, trisodium

EXAMPLE 8

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(cirullinato-N)-, trisodium

EXAMPLE 9

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(argininato-N)-, trisodium

EXAMPLE 10

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(phenylalaninato-N)-, trisodium

EXAMPLE 11

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(tyrosinato-N)-, trisodium

EXAMPLE 12

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(threoninato-N)-, trisodium

EXAMPLE 13

Cobaltate(3-), [7,12-diethyl-3,8,13,17-tetramethyl-21H,23H-porphine-2,18-dipropanoato(4-)-N$^{21}$,N$^{22}$, N$^{23}$,N$^{24}$]-bis(leucinato-N)-, trisodium

EXAMPLE 14

Cobaltate(3-), [7,12-diethyl-3,8,13,17-tetramethyl-21H,23H-porphine-2,18-dipropanoato(4-)-$N^{21}$,$N^{22}$,$N^{23}$,$N^{24}$]-bis(isoleucinato-N)-, trisodium

EXAMPLE 15

Cobaltate(3-), [7,12-diethyl-3,8,13,17-tetramethyl-21H,23H-porphine-2,18-dipropanoato(4-)-$N^{21}$,$N^{22}$,$N^{23}$,$N^{24}$]-bis(valinato-N)-, trisodium

EXAMPLE 16

Cobaltate(3-), [7,12-diethyl-3,8,13,17-tetramethyl-21H,23H-porphine-2,18-dipropanoato(4-)-$N^{21}$,$N^{22}$,$N^{23}$,$N^{24}$]-monoacuato mono(glycinate-N)-, disodium

EXAMPLE 17

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(glycinato-N)-, trihydrogen

EXAMPLE 18

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(alaninato-N)-, trisodium

EXAMPLE 19

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(serinato-N)-, trisodium

EXAMPLE 20

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(lysinato-N)-, trisodium

EXAMPLE 21

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(ornithinato-N)-, trisodium

EXAMPLE 22

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(cirullinato-N)-, trisodium

EXAMPLE 23

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(argininato-N)-, trisodium

EXAMPLE 24

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(phenylalaninato-N)-, trisodium

EXAMPLE 25

Cobaltate(3-) [7,12-diethenyl-3,8,13,17-tetramethyl-21H,23H-porphine-2,18-dipropanoato(4-)-$N^{21}$,$N^{22}$,$N^{23}$,$N^{24}$]-bis(tyrosinato-N)-, trisodium

EXAMPLE 26

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(threoninato-N)-, trisodium

EXAMPLE 27

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(leucinato-N)-, trisodium

EXAMPLE 28

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(isoleucinato-N)-, trisodium

EXAMPLE 29

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(valinato-N)-, trisodium

EXAMPLE 30

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-bis(tryptophanato-N)-, trisodium

EXAMPLE 31

Cobaltate(3-), [7,12-diethenyl-3,8,13,17-tetramethyl-21H,23H-porphine-2,18-dipropanoato(4-)-$N^{21}$,$N^{22}$,$N^{23}$,$N^{24}$]-monoaquato mono(glycinato-N)-, disodium

EXAMPLE 32

Cobaltate(3-), [7,12-diethyl-3,8,13,17-tetramethyl-21H,23H-porphine-2,18-dipropanoato-(4-)-$N^{21}$,$N^{22}$,$N^{23}$,$N^{24}$]-bis(glycinato-N)-, trihydrogen.

EXAMPLE 33

Cobaltate(3-), [7,12-diethyl-3,8,13,17-tetramethyl-21H,23H-porphine-(2-)-$N^{21}$,$N^{22}$,$N^{23}$,$N^{24}$-2,18-dipropanic acid]-bis(tryptophanato-N)-, (CoMP.2Trp)

A formulated mixture of Cobaltate(3-), [7,12-diethyl-3,8,13,17-tetramethyl-21H,23H-porphine-2,18-dipropanoato (4-)-$N^{21},N^{22},N^{23},N^{24}$]-bis(glycinato-N)-, trisodium (Example 1) ($Na_3COMP.2Gly$) (2.00 g, equivalent to 1.8 mmol $Co^{III}MP.2Gly$) (also containing glycine (1.8 mmol), $NaH_2PO_4$ (0.9 mmol) and $Na_2HPO_4$ (0.9 mmol)) and L-tryptophan (2.00 g, 9.8 mmol) were heated at 50° C. in water (150 mL) for 30 minutes. The solution was cooled to room temperature and 1M hydrochloric acid (18 mL, 18 mmol) was added. The precipitate was filtered off and washed with water (3×20 mL). The residual solid was dissolved in water (150 mL) with trisodium phosphate dodecahydrate (1.5 g, approx. 4 mmol) and L-tryptophan (1.5 g, 7.3 mmol), and heated at 50° C. for 30 minutes (vigorous stirring to ensure complete dissolution is recommended). The cooled solution was filtered (medium glass frit). The solution was rapidly acidified with 1M hydrochloric acid (25 mL), and the precipitate was filtered on a fine glass filter. The solid was washed with water until the filtrate was neutral. The solid residue was sucked dry on the filter, then vacuum dried at up to 90° C. (1 mm·Hg) to afford the CoMP.2Trp as the free acid (1.57 g, 83% yield).

Calculated for $C_{56}H_{59}N_8O_8Co_1 \cdot 0.7H_2O$: C, 64.44; H, 5.83; N, 10.74; Co, 5.65; $H_2O$, 1.2% (FW=1043). Found: C, 64.19; H, 5.60; N, 10.70; Co, 5.44; $H_2O$, 0.80%.

$^1$H NMR (10.4 mg in $D_2O$ (1 mL) and $K_2CO_3$ (9 mg) with p-dioxane (~0.5 μL) referenced to δ 3.70): δ 10.13 (s, 1H), 10.07 (s, 1H), 10.0 (s, 1H), 9.71 (s, 1H), 7.50 (dd, J=8, 2 Hz, 2H), 7.30 (m, 2H), 6.72 (m, 2H), 5.34 (d, J=8 Hz, 1H), 5.30 (d, J=8 Hz, 1H), 4.89 (s, 1H), 4.87 (s, 1H), 4.3 (m, 4H), 4.05 (m, 4H), 3.61 (s, 3H), 3.57 (s, 3H), 3.51 (s, 6H), 3.14 (q, J=8.2 Hz, 4H), 1.87 (t, J=8.2 Hz, 3H), 1.83 (t, J=8.2 Hz, 3H), 0.22 (br. d, J=15 Hz, 2H), -0.72 (dd, J=15, 12 Hz, 2H), -5.05 (dd reduced to d after complete NH/ND exchange, J=12, 10 Hz, 2H), -5.68 (t, J=10 Hz, 2H that disappear with $t_{1/2}$ of 150 min at 20° C., NH), -6.67 (d, J=10 Hz, 2H that disappear with $t_{1/2}$ of 120 min at 22° C., NH).

EXAMPLE 34

Cobaltate(3-) [7,12-diethyl-3,8,13,17-tetramethyl-21H,23H-porphine-2,18-dipropanoato-(4))-$N^{21},N^{22},N^{23},N^{24}$]-bis(tryptophanato-N)-, trisodium ($Na_3CoMP.2Trp$)

CoMP.2Trp (53 mg, 0.051 mmol), trisodium phosphate dodecahydrate (39 mg, 0.102 mmol) and L-tryptophan (5 mg, 0.025 mmol) were mixed in water (3.15 mL) and sonicated in a water bath for 10 minutes. As prepared, the solution had pH 7.52. The solution may be filter sterilized and lyophilized.

What is claimed is:

1. A compound of Formula I

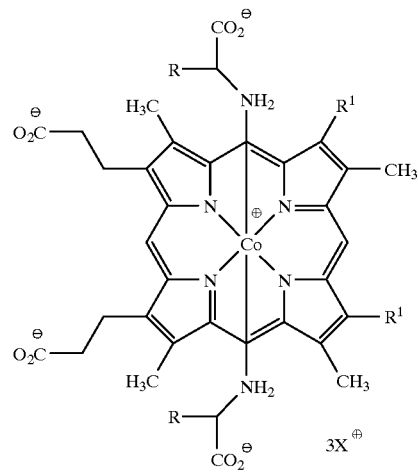

wherein R is H, alkyl, alkenyl, cycloalkyl, cycloalkylalkyl, aryl, arylalkyl, heteroaryl, heteroarylalkyl, —$(CH_2)_n$—$R^2$ wherein $R^2$ is

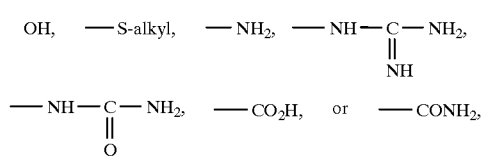

and n is zero or an integer of 1 to 4, or

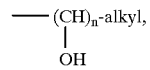

wherein n is as defined above;

$R^1$ is —$CH_2CH_3$ or —$CH=CH_2$; and

X is hydrogen or a pharmaceutically acceptable cation.

2.

A compound of Formula II

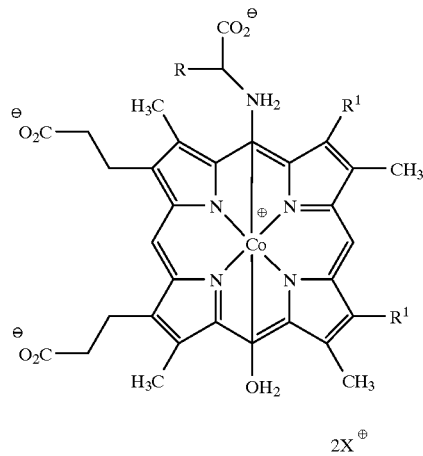

wherein R is

H, alkyl, alkenyl, cycloalkyl, cycloalkylalkyl, aryl, arylalkyl, heteroaryl, heteroarylalkyl, —$(CH_2)_n$—$R^2$ wherein $R^2$ is OH, —S-alkyl, —$NH_2$, —NH—C(=NH)—$NH_2$, —NH—C(=O)—$NH_2$, —$CO_2H$, or —$CONH_2$, and n is zero or an integer of 1 to 4, or —CH(OH)—$(CH)_n$-alkyl, wherein n is as defined above;
$R^1$ is —$CH_2CH_3$ or —CH=$CH_2$; and
X is hydrogen or a pharmaceutically acceptable cation.

3. A compound according to claim 1 wherein R is

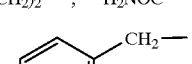

4. A compound according to claim 3 wherein R is

H, $CH_3$—, $(H_3C)_2$—CH—, $(H_3C)_2$—CH—$CH_2$—, $H_3C$—$CH_2$—CH($CH_3$)—, HO—$CH_2$—, $H_3C$—CH(OH)—, $H_2N$—$(CH_2)_3$—, $H_2N$—$(CH_2)_4$—, $H_2N$—C(=NH)—NH—$(CH_2)_3$—, $H_2N$—CONH—$(CH_2)_3$—,

[benzyl, 4-hydroxybenzyl, 3,4-dihydroxybenzyl, indol-3-ylmethyl, 5-hydroxyindol-3-ylmethyl structures]

5. A compound according to claim 4 selected from the group consisting of:

Cobaltate(3-), [7,12-diethyl-3,8,13,17-tetramethyl-21H,23H-porphine-2,18-dipropanoato-(4-)-$N^{21}$,$N^{22}$,$N^{23}$,$N^{24}$]-bis(glycinato-N)-, trisodium;

Cobaltate(3-), [7,12-diethyl-3,8,13,17-tetramethyl-21H,23H-porphine- 2,18-dipropanoato-(4-)-$N^{21}$,$N^{22}$,$N^{23}$,$N^{24}$]-bis(glycinato-N)-, trihydrogen;

Cobaltate(3-), [7,12-diethyl-3,8,13,17-tetramethyl-21H,23H-porphine-2,18-dipropanoato(4-)-$N^{21}$,$N^{22}$,$N^{23}$,$N^{24}$]-bis(alaninato-N)-, trisodium;

Cobaltate(3-), [7,12-diethyl-3,8,13,17-tetramethyl-21H,23H-porphine-2,18-dipropanoato-(4-)-$N^{21}$,$N^{22}$,$N^{23}$,$N^{24}$]-bis(serinato-N)-, trisodium;

Cobaltate(3-), [7,12-diethyl-3,8,13,17-tetramethyl-21H,23H-porphine-2,18-dipropanoato(4-)-$N^{21}$,$N^{22}$,$N^{23}$,$N^{24}$]-bis(lysinato-N)-, trisodium;

Cobaltate(3-), [7,12-diethyl-3,8,13,17-tetramethyl-21H,23H-porphine-2,18-dipropanoato-(4-)-$N^{2}1$,$N^{22}$,$N^{23}$,$N^{24}$]-bis(ornithinato-N)-, trisodium;

Cobaltate(3-), [7,12-diethyl-3,8,13,17-tetramethyl-21H,23H-porphine-2,18-dipropanoato-(4-)-$N^{21}$,$N^{22}$,$N^{23}$,$N^{24}$]-bis(cirullinato-N)-, trisodium;

Cobaltate(3-), [7,12-diethyl-3,8,13,17-tetramethyl-21H,23H-porphine-2,18-dipropanoato-(4-)-$N^{21}$,$N^{22}$,$N^{23}$,$N^{24}$]-bis(argininato-N)-, trisodium;

Cobaltate(3-), [7,12-diethyl-3,8,13,17-tetramethyl-21H, 23H-porphine-2,18-dipropanoato-(4-) -N²¹,N²²,N²³, N²⁴]-bis(phenylalaninato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(tyrosinato-N)-, trisodium;

Cobaltate(3-), [7,12-diethyl-3,8,13,17-tetramethyl-21H, 23H-porphine-2,18-dipropanoato-(4-) -N²¹N²²,N²³, N²⁴]-bis(3-hydroxytyrosinato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(threoninato-N)-, trisodium;

Cobaltate(3-), [7,12-diethyl-3,8,13,17-tetramethyl-21H, 23H-porphine-2,18-dipropanoato-(4-)-N²¹N²²,N²³, N²⁴]-bis(leucinato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(isoleucinato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(valinato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(tryptophanato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(5-hydroxytryptophanato-N)-, trisodium;

Cobaltate(3-), [7,12-diethenyl-3,8,13,17-tetramethyl-21H,23H-porphine-2,18-dipropanoato-(4-) -N²¹,N²², N²³,N²⁴]-bis(glycinato-N)-, trihydrogen;

Cobaltate(3-), [7,12-diethenyl-3,8,13,17-tetramethyl-21H,23H-porphine-2,18-dipropanoato-(4-)-N²¹N²², N²³,N²⁴]-bis(alaninato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(serinato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(lysinato-N)-, trisodium;

Cobaltate(3-), [7,12-diethenyl-3,8,13,17-tetramethyl-21H, 23H-porphine-2,18-dipropanoato(4-)-N²¹,N²², N²³,N²⁴]-bis(ornithinato-N)-, trisodium;

Cobaltate(3-), [7,12-diethenyl-3,8,13,17-tetramethyl-21H,23H-porphine-2,18-dipropanoato-(4-) -N²¹,N²², N²³,N²⁴]-bis(cirullinato-N)-, trisodium;

Cobaltate(3-), [7,12-diethenyl-3,8,13,17-tetramethyl-21H,23H-porphine-2,18-dipropanoato-(4-)-N²¹N²², N²³,N²⁴]-bis(argininato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(phenylalaninato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(tyrosinato-N)-, trisodium;

Cobaltate(3-), [7,12-diethenyl-3,8,13,17-tetramethyl-21H,23H-porphine-2,18-dipropanoato-(4-)-N²¹l,N²², N²³,N²⁴]-bis(3-hydroxytyrosinato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(threoninato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(leucinato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(isoleucinato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(valinato-N)-, trisodium;

Cobaltate(3-), [7,12-diethenyl-3,8,13,17-tetramethyl-21H,23H-porphine-2,18-dipropanoato-(4-)-N²¹,N²², N²³,N²⁴]-bis(tryptophanato-N)-, trisodium; and Cobaltate(3-), [7,12-diethenyl-3,8,13,17-tetramethyl-21H, 23H-porphine-2,18-dipropanoato(4-)-N²¹,N²², N²³,N²⁴]-bis(5-hydroxytryptophanato-N)-, trisodium.

6. A compound according to claim 5 which is

Cobaltate(3-), [7,12-diethyl-3,8,13,17-tetramethyl-21H, 23H-porphine-2,18-dipropanoato-(4-)-N²¹,N²²,N²³, N²⁴]-bis(glycinato-N)-, trisodium;

Cobaltate(3-), [7,12-diethyl-3,8,13,17-tetramethyl-21H, 23H-porphine-2,18-dipropanoato-(4-)-N²¹,N²²,N²³, N²⁴]-bis(tryptophanato-N)-, trisodium; and Cobaltate(3-), [7,12-diethyl-3,8,13,17-tetramethyl-21H, 23H-porphine-2,18-dipropanoato-(4-)-N²¹,N²²,N²³, N²⁴]-bis(5-hydroxytryptophanato-N)-, trisodium.

7. A compound according to claim 2 wherein R is

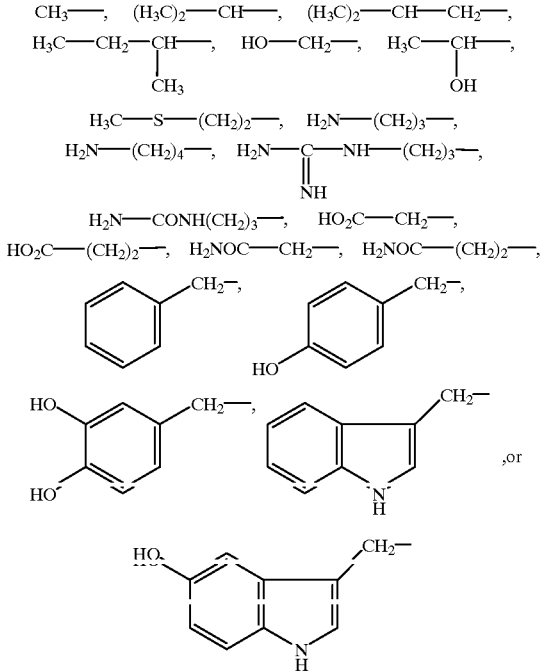

8. A compound according to claim 7 wherein R is

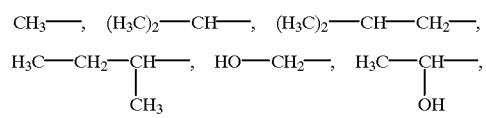

-continued

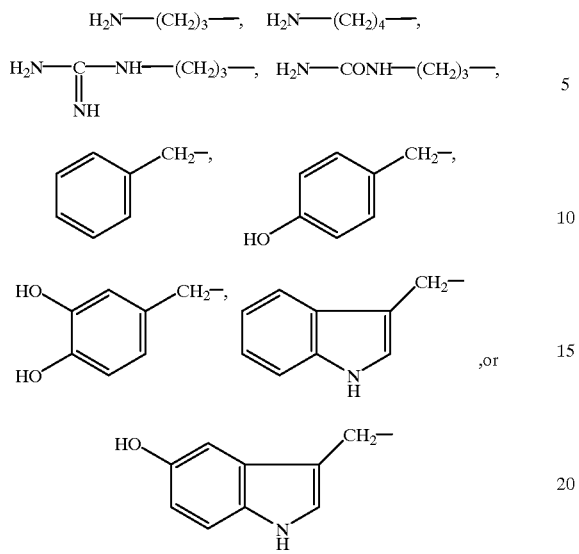

9. A compound according to claim 8 which is selected from the group consisting of:

Cobaltate(3-), [7,12-diethyl-3,8,13,17-tetramethyl-21H, 23H-porphine-2,18-dipropanoato(4-)-$N^{21},N^{22},N^{23}, N^{24}$]-monoaquato mono(glycinato-N)-, disodium; and Cobaltate(3-), [7,12-diethenyl-3,8,13,17-tetramethyl-21H,23H-porphine-2,18-dipropanoato-(4-)-$N^{21},N^{22}, N^{23},N^{24}$]-monoaquato mono(glycinato-N)-, disodium.

10. A method of treating obesity comprising administering to a host suffering therefrom a therapeutic effective amount of a compound according to claim 1 in unit dosage form.

11. A method of treating obesity comprising administering to a host suffering therefrom a therapeutically effective amount of a compound according to claim 2 in unit dosage form.

12. A pharmaceutical composition comprising a compound according to claim 1 in admixture with a pharmaceutically acceptable excipient, diluent, or carrier.

13. A pharmaceutical composition adapted for administration as an agent for treating obesity comprising a therapeutically effective amount of a compound according to claim 1 in admixture with a pharmaceutically acceptable excipient, diluent, or carrier.

14. A pharmaceutical composition adapted for administration as an agent for treating obesity comprising a therapeutically effective amount of a compound according to claim 2 in admixture with a pharmaceutically acceptable excipient, diluent, or carrier.

15. A method of preparing a compound of Formula I

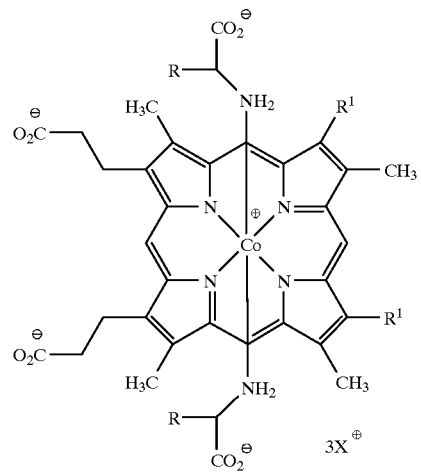

wherein R is H,
alkyl,
alkenyl,
cycloalkyl,
cycloalkylalkyl,
aryl,
arylakyl,
heteroaryl,
heteroarylalkyl,
—$(CH_2)_n$—$R^2$ wherein $R^2$ is OH,
—S-alkyl,
—$NH_2$,

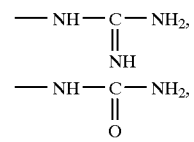

—$CO_2H$, or
—$CONH_2$, and
n is zero or an integer of 1 to 4, or

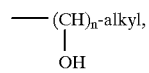

wherein n is as defined above;
$R^1$ is —$CH_2CH_3$ or —$CH=CH_2$; and
X is hydrogen or a pharmaceutically acceptable cation comprising reaction of a compound of Formula III

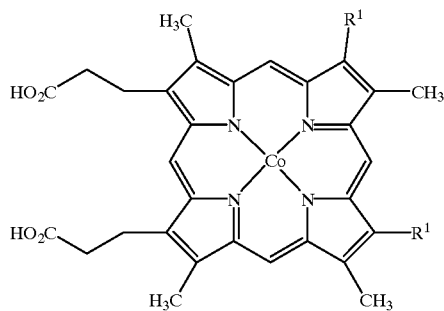

wherein $R^1$ is as defined above and two or more equivalents of a compound of Formula IV

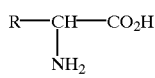

wherein R is as defined above and three or more equivalents of a base in a solvent under an air or oxygen atmosphere to affect dissolution and to afford after filtration and lyophilization a compound of Formula I.

16. A method of preparing a compound of Formula II

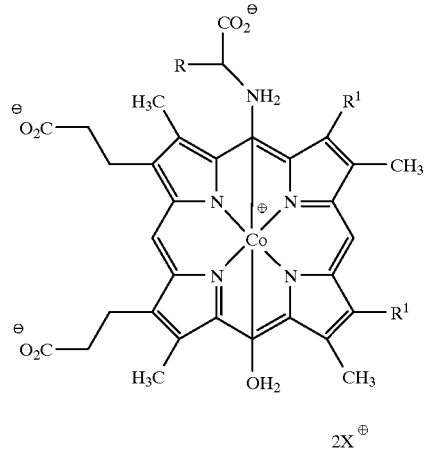

wherein R is H, alkyl, alkenyl, cycloalkyl, cycloalkylalkyl, aryl, arylalkyl, heteroaryl, heteroarylalkyl, —$(CH_2)_n$—$R^2$ wherein $R^2$ is OH, —S-alkyl,

—$NH_2$,

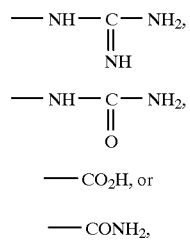

—$CO_2H$, or

—$CONH_2$, and n is zero or an integer of 1 to 4, or

—(CH)$_n$-alkyl,   wherein n is as defined above;
 |
 OH $R^1$ is —$CH_2CH_3$ or —$CH=CH_2$; and X is hydrogen or a pharmaceutically acceptable cation comprising adjusting the pH of an aqueous solution of a compound of Formula I to afford a compound of Formula II.

* * * * *

UNITED STATES PATENT AND TRADEMARK OFFICE
CERTIFICATE OF CORRECTION

PATENT NO. : 5,929,064
DATED : JULY 27, 1999
INVENTOR(S) : GOEL ET AL.

It is certified that error appears in the above-identified patent and that said Letters Patent is hereby corrected as shown below:

Col. 5, line 58: insert --R is-- at beginning of line

Col. 9, line 20: "tetrameethyl" should read --tetramethyl--

Col. 22, line 60, claim 5: "$N^21$" should read --$N^{21}$--

Col. 23, line 62, claim 5: "$N^21$" should read --$N^{21}$--

Col. 24, line 60, claim 8: Insert --H,-- after the word "is"

Signed and Sealed this

Eighth Day of May, 2001

*Attest:*

NICHOLAS P. GODICI

*Attesting Officer*    *Acting Director of the United States Patent and Trademark Office*